United States Patent
Aprile

(10) Patent No.: US 10,905,892 B2
(45) Date of Patent: Feb. 2, 2021

(54) PORTABLE MONITORED AED SYSTEM AND STREET FURNITURE FOR AN AED

(71) Applicant: Zapstand, LLC, Dallas, TX (US)

(72) Inventor: Reno Aprile, Terrey Hills (AU)

(73) Assignee: ZAPSTAND, LLC, Dallas, TX (US)

( * ) Notice: Subject to any disclaimer, the term of this patent is extended or adjusted under 35 U.S.C. 154(b) by 0 days.

(21) Appl. No.: 16/405,299

(22) Filed: May 7, 2019

(65) Prior Publication Data
US 2020/0054885 A1 Feb. 20, 2020

Related U.S. Application Data

(60) Provisional application No. 62/719,024, filed on Aug. 16, 2018.

(51) Int. Cl.
*G08B 1/08* (2006.01)
*A61N 1/39* (2006.01)
(Continued)

(52) U.S. Cl.
CPC ............ *A61N 1/3925* (2013.01); *A61N 1/08* (2013.01); *A61N 1/3904* (2017.08);
(Continued)

(58) Field of Classification Search
None
See application file for complete search history.

(56) References Cited

U.S. PATENT DOCUMENTS 6,301,501 B1  10/2001  Cronin et al.
6,662,046 B2 * 12/2003  Hansen ................. A61N 1/39
                                                              607/5

(Continued)

FOREIGN PATENT DOCUMENTS

AU  2007203529 A1  6/2008
CH      708729 A2  5/2015
(Continued)

OTHER PUBLICATIONS

Pyres; AIVIA—Cabinet Ranges for Automated External Defibrillators (AED); www.pyres.com/solutions/aivia.
(Continued)

*Primary Examiner* — Julie B Lieu
(74) *Attorney, Agent, or Firm* — Clark Hill PLC; James R. Foley

(57) ABSTRACT

A smart carry case which is effectively a portable GPS-enabled, AED monitoring system that is capable of monitoring an AED (as well as itself) and reporting back the presence, function and location of the AED to a remote host. Also disclosed is street furniture that is configured to retain, continuously monitor, and dispense an AED and communicate to a remote host (i.e., a control room). The street furniture is preferably configured such that a user presses the intercom button. In response, the street furniture contacts the control room. The control room, in turn, sends a signal to the street furniture causing the compartment to unlock so the AED can be removed and used in a rescue. The street furniture is configured to continuously monitor the AED and ensure it is functional, using a device such as has been described hereinabove. If the AED is used, an ambulance is deployed to the location. The AED that is retained in the compartment may be a smart carry case. As such, the presence, function, and location of the AED can be continuously monitored.

20 Claims, 9 Drawing Sheets

(51) Int. Cl.
*G16H 40/67* (2018.01)
*G07C 9/00* (2020.01)
*G07C 9/38* (2020.01)
*A61N 1/08* (2006.01)

(52) U.S. Cl.
CPC ......... *A61N 1/3968* (2013.01); *A61N 1/3993* (2013.01); *G07C 9/00571* (2013.01); *G07C 9/00896* (2013.01); *G07C 9/38* (2020.01); *G16H 40/67* (2018.01)

(56) References Cited

U.S. PATENT DOCUMENTS

| | | | |
|---|---|---|---|
| 6,727,814 B2 | 4/2004 | Saltzstein et al. | |
| 6,735,473 B2 | 5/2004 | Kolder et al. | |
| 8,960,430 B2 | 2/2015 | Roach et al. | |
| 2003/0114885 A1* | 6/2003 | Nova | A61N 1/046 607/2 |
| 2003/0212311 A1 | 11/2003 | Nova et al. | |
| 2004/0124979 A1 | 7/2004 | Medema et al. | |
| 2006/0100530 A1 | 5/2006 | Kliot et al. | |
| 2007/0032830 A1* | 2/2007 | Bowers | A61N 1/39 607/5 |
| 2011/0163881 A1 | 7/2011 | Halff et al. | |
| 2014/0266718 A1 | 9/2014 | Bongberg et al. | |
| 2015/0231404 A1 | 8/2015 | Baucom et al. | |
| 2015/0297906 A1 | 10/2015 | Guichet | |
| 2016/0045753 A1 | 2/2016 | Axness | |
| 2016/0166349 A1 | 6/2016 | Guichet | |
| 2016/0295114 A1 | 10/2016 | Finch et al. | |
| 2016/0374894 A1* | 12/2016 | Freeman | A61H 31/005 601/18 |
| 2017/0028211 A1 | 2/2017 | Tilton, Jr. | |
| 2017/0281016 A1* | 10/2017 | Elghazzawi | H04N 7/181 |
| 2018/0369598 A1* | 12/2018 | Newton | A61N 1/3904 |

FOREIGN PATENT DOCUMENTS

| | | |
|---|---|---|
| CN | 207117964 U | 3/2018 |
| CN | 207558176 U | 6/2018 |
| JP | 2013078548 A | 5/2013 |
| KR | 101025295 B1 | 3/2011 |
| KR | 10-2011-0066459 A | 6/2011 |
| KR | 10-2013-0016887 A | 2/2013 |
| KR | 101291415 B1 | 7/2013 |
| KR | 20150062430 A | 6/2015 |
| KR | 20180043164 A | 4/2018 |
| WO | 2017/162627 A1 | 9/2017 |

OTHER PUBLICATIONS

Emergency Focus; Console AED Proximus®; www.emergencyfocus.com/products-aed-defibrillator-remote-control.html.
AEDMap; HS1 Wireless Monitoring Cabinet; https://aedmap.org/wp-content/uploads/2015/10/HS1-Monitored-Cabinet.pdf.
Eiremed; AED Cabinet With Alarm; https://eiremed.ie/product/aed-cabinet-with-alarm/.
Eiremed; Durafib, Outdoor Polycarbonate, Digital Heated AED Cabinet With Lock; https://eiremed.ie/product/durafib-outdoor-polycarbonate-digital-heated-aed-cabinet-with-lock/.
HeartSine; HeartSine Samaritan® PAD Family; https://heartsinelive.s3.amazonaws.com/uploads/2015/06/0118_H009-032-223-3_US_AccessoryFlyer_web.pdf.
Laudren Electronic; AED Connected Wall Box; https://partners.sigfox.com/products/aed-connected-wall-box.

* cited by examiner

PORTABLE MONITORED AED SYSTEM AND STREET FURNITURE FOR AN AED

RELATED APPLICATION (PRIORITY CLAIM)

This application claims the benefit of U.S. Provisional Application Ser. No. 62/719,024, filed Aug. 16, 2018, which is hereby incorporated herein by reference in its entirety.

BACKGROUND

The present invention generally relates to methods and systems for providing access to medical devices, and more specifically relates to a portable monitored Automated External Defibrillator (AED) system.

Sudden cardiac arrest occurs when victims have an abnormal heart rhythm called ventricular fibrillation. In this state, the heart cannot beat in a coordinated fashion and blood does not circulate to the heart and the brain. The victim loses consciousness, collapses and appears lifeless. Ventricular fibrillation is a treatable arrhythmic condition. Electrical energy is present in the heart, but is chaotic. The treatment for most cases of sudden cardiac arrest is treatment with a defibrillator to shock the heart out of a fatal rhythm, allowing a normal, healthy rhythm to resume. Although AED's are safe, effective and easily applied, few victims of sudden cardiac arrest have ready access to AED's.

The shorter the time from collapse to defibrillation, the better the chances of survival. If defibrillation is applied within 1-2 minutes, survival rates of 90% have been reported. If defibrillation is applied after 6 minutes, the survival rate is about 45%. Where defibrillation is delayed by more than 10 minutes, the survival rate drops to less than 5%.

Although most victims of sudden cardiac arrest are middle-aged or elderly, many victims are in their thirties. Cardiac arrest may occur at any location, for example at home, in shopping centres, on public transport or at work. Consequently, the widespread availability of AED's at workplaces and in the broader community would be beneficial in addressing the problem of sudden cardiac arrest. There is a need for the widespread provision of AED's to improve the chances of victims surviving sudden cardiac arrest.

In addition to the requirement for widespread provision of AED's, there is also a requirement to ensure that the AED's that are distributed are safe and reliable. The potential for liability associated with AED ownership may limit the ability to achieve widespread provision of AED's. The annual number of AED's distributed between 1996 and 2005 increased almost ten-fold. During that period, the U.S. Food and Drug Administration (FDA) issued 52 advisories involving either AEDs or critical AED accessories. FDA data showed that during this 10-year period, many AED's were recalled due to the potential to malfunction.

The components of a standard AED 50 are shown in the block diagram of FIG. 1. The AED 50 includes electrodes 51 that, in use, are applied to a patient. The AED 50 is a portable device that is powered by battery 53. The operation of the AED 50 is controlled by electronic circuitry 52. A watchdog unit 54 monitors the status of the AED 50. If faults are detected by the watchdog unit 54, an audible alarm indicator 55 is activated to emit an audible alarm.

Some AED's are GPS-enabled. FIG. 2 shows a schematic block diagram of a GPS-enabled AED 60. The three principal components of a GPS-enabled AED 60 are a standard AED 50, a GPS device 61 and a two-way communicator 62. The components 50, 61 and 62 may be standard devices. The combination of the AED 50 and the GPS device 61 permits tracking of the location of the AED, and may facilitate recovery in the event of theft, or assist in the accurate dispatch of a rescuer or ambulance. The two-way communicator 62 may provide communication between the user and, for example, rescuers or ambulance personnel. The GPS-enabled AED 60 is typically a wall-mounted unit, and the entire wall-mounted unit must be removed from the wall in order to use the standard AED 50 component of the system. Additionally, once the GPS-enabled AED 60 is removed from the wall, the battery 53 of the AED 50 is forced to power all the functions of the GPS-enabled AED 60. Furthermore, the GPS-enabled AED 60 does not include any first aid supplies despite the fact that certain first aid supplies might be very helpful to have at the scene at which the GPS-enabled AED 60 is being used.

SUMMARY

An object of an embodiment of the present invention is to provide a smart carry case for an AED Another object of an embodiment of the present invention is to provide a smart carry case for an AED that enables continuous monitoring of an AED, and reporting to a remote host, without drawing on the battery of the AED.

Briefly, an embodiment of the present invention provides a smart carry case for an AED that is configured to contain an AED, a mobile AED monitoring and alerting device which is configured to continuously monitor the AED and communicate to a remote host, and first aid supplies. The AED can be conventional and is removable from the smart carry case, along with the first aid supplies which can also be conventional. The mobile AED monitoring and alerting device may include, among other components, a battery which powers the device, a socket for charging the battery, a GPS device that permits tracking of the location of the device, an audio detector (i.e., microphone and associated processor) which continuously listens for alarms being emitted from the AED, at least one accelerometer for detecting movement of the device, and a speaker or buzzer for emitting an audible alarm. Preferably, the smart carry case is durable and includes a formed insert which is configured to effectively organize the contents of the smart carry case (i.e., the AED, the mobile AED monitoring and alerting device, and first aid supplies).

Another embodiment of the present invention provides street furniture that is configured to retain, continuously monitor, and dispense an AED and communicate to a remote host (i.e., a control room). The street furniture may include, among other components, a lockable compartment for containing the AED, an intercom panel (i.e., a button, at least one speaker and a microphone), and at least one surveillance camera. The street furniture may also include a digital display, such as illuminated signage. The street furniture is preferably configured such that a user presses the intercom button. In response, the street furniture contacts the control room. The control room, in turn, may remotely unlock the compartment as an extra security precaution for the AED to be taken and used in a rescue. The street furniture is configured to continuously monitor the AED and ensure it is functional. If the AED is used, an ambulance is deployed to the location. The AED which is dispensed by the street furniture could be the smart carry case which has been described previously.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which.

DESCRIPTION OF ILLUSTRATED EMBODIMENTS

Figure 1:
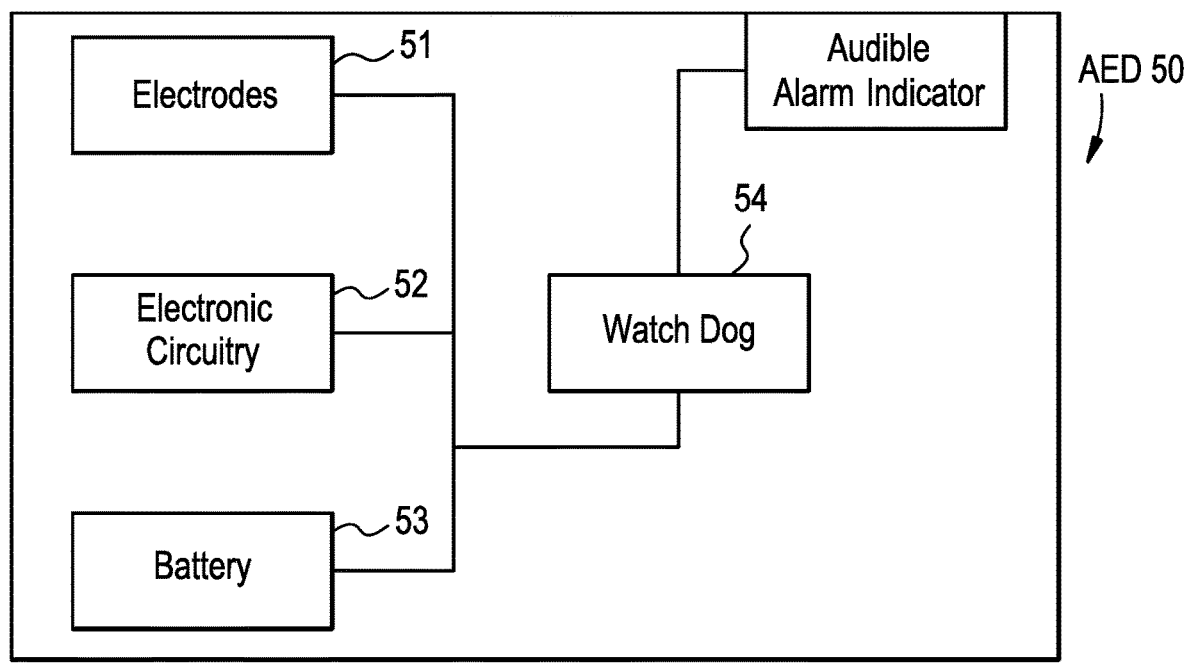
FIG. 1 is a schematic block diagram of a conventional AED.
Figure 2:
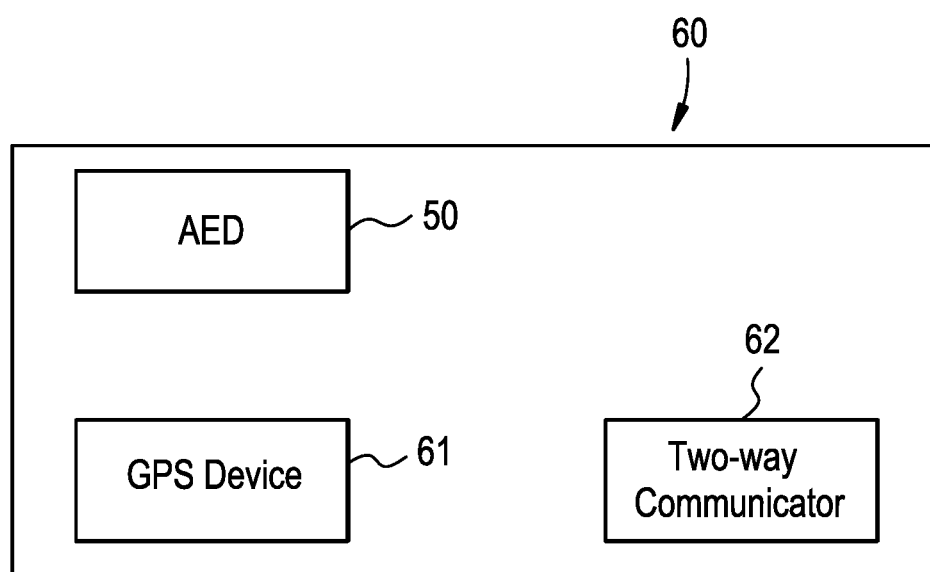
FIG. 2 is a schematic block diagram of a conventional GPS-enabled AED.

While this invention may be susceptible to embodiment in different forms, there are shown in the drawings and will be described herein in detail, specific embodiments with the understanding that the present disclosure is to be considered an exemplification of the principles of the invention, and is not intended to limit the invention to that as illustrated.

Figure 3:
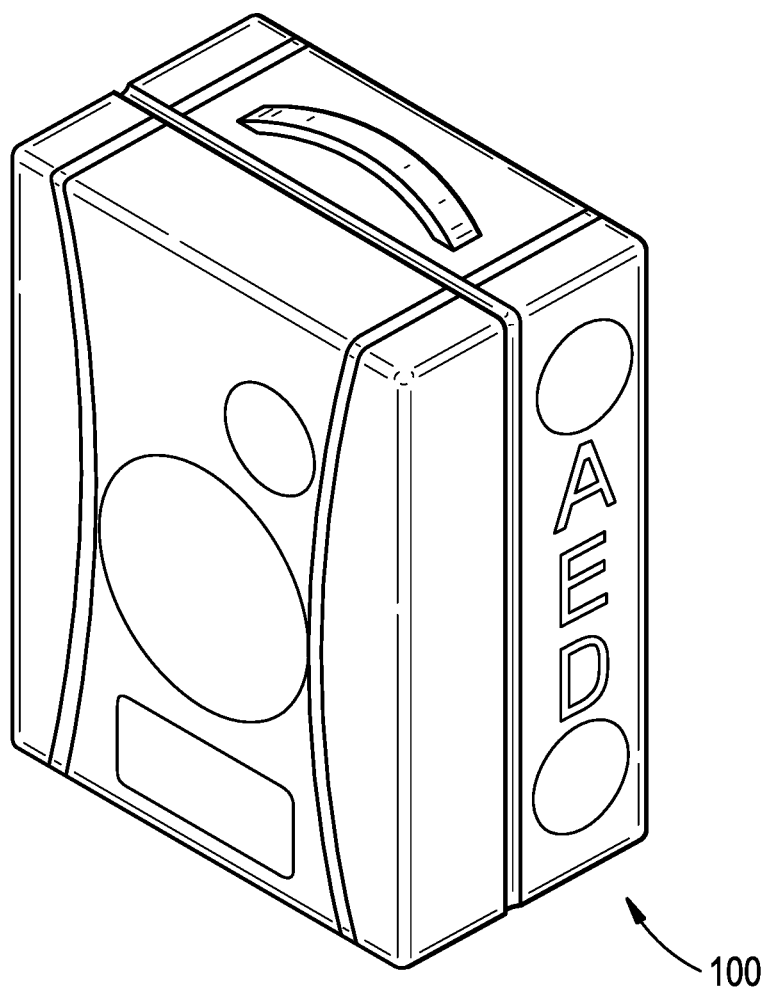
FIG. 3 is a perspective view of a smart carry case that is in accordance with an embodiment of the present invention.

FIG. 3 is a perspective view of a smart carry case 100 that is in accordance with an embodiment of the present invention. The smart carry case 100 is preferably durable, waterproof, and has high visibility.

Figure 4:
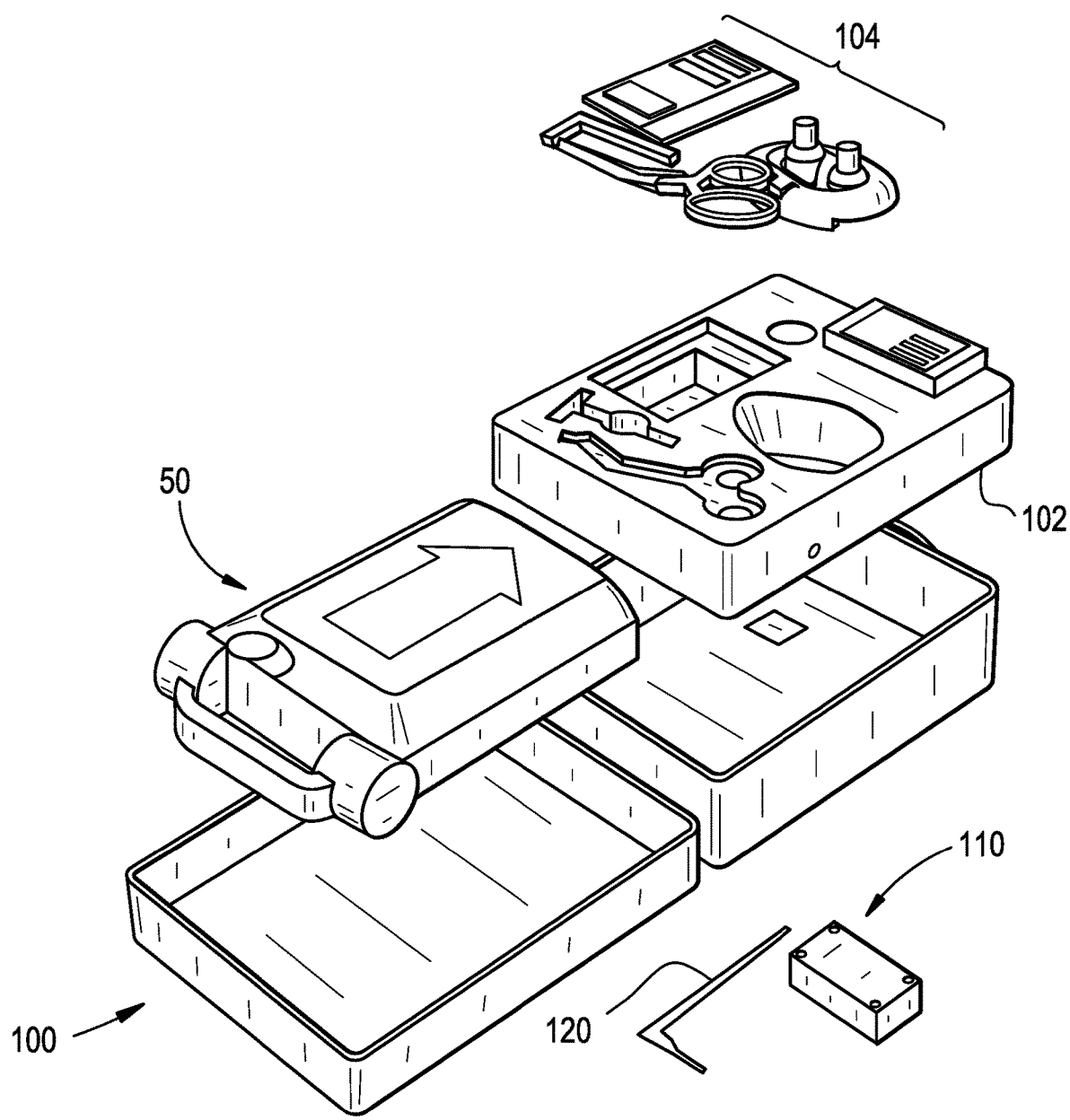
FIG. 4 is an exploded perspective view showing internal components of the smart carry case shown in FIG. 3.

FIG. 4 is an exploded perspective view showing internal components of the smart carry case 100 shown in FIG. 3. As shown, preferably the internal contents include a conventional AED 50 which is disposed on one side, inside the smart carry case 100, and a formed insert 102 which is disposed on the other side, inside the smart carry case. The formed insert 102 is preferably configured to keep organized first aid supplies 104 such as scissors, razor, swabs and gloves, a mask, etc. which a user can use in connection with using the conventional AED 50.

Preferably, a mobile AED monitoring and alerting device 110 is disposed under the formed insert 102, out of view from the user, which functions to continuously monitor the presence, function, and location of the AED 50. The device 110 renders the smart carry case 100 a portable GPS-enabled, AED monitoring system that is capable of monitoring an AED 50 and reporting back the presence, function and location of the AED to a remote host 112 (See FIG. 6). As will be described, the device 110 also continuously monitors certain things about itself as well, and reports back to a remote host 112 (see FIG. 6) and/or emits an audible alarm.

Figure 5:
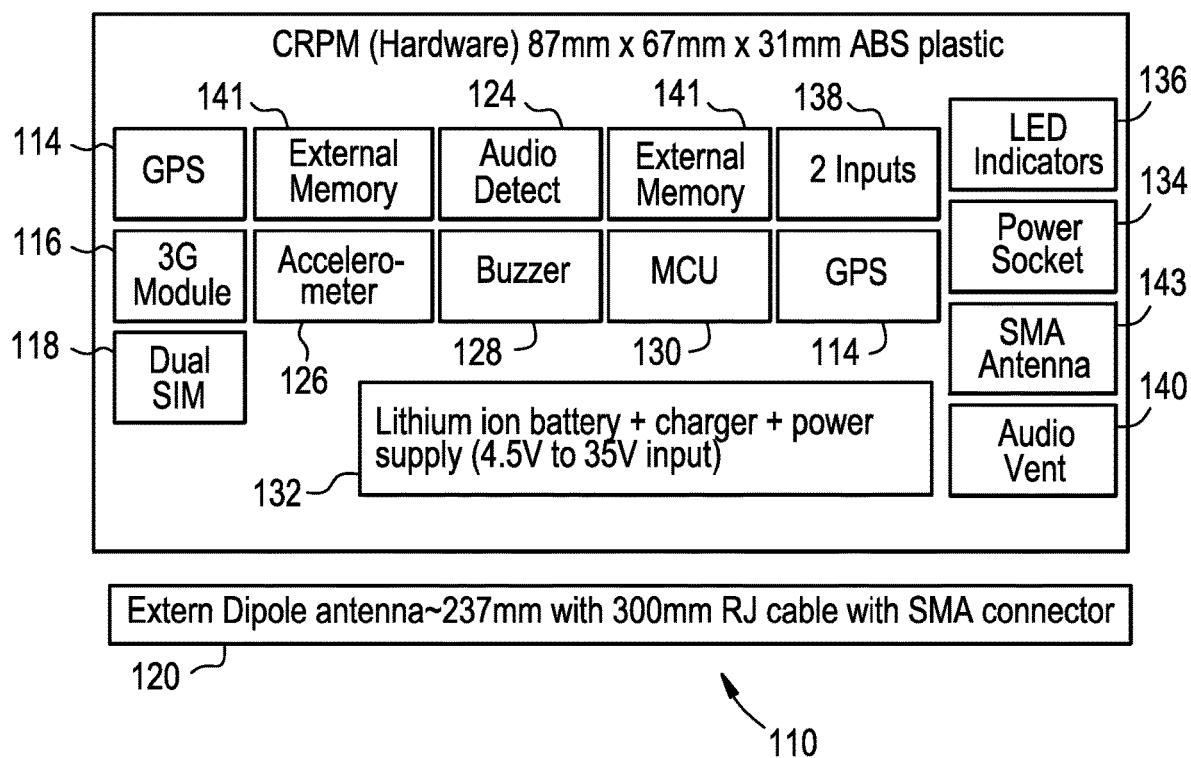
FIG. 5 is a schematic block diagram of a mobile AED monitoring and alerting device that is contained in the smart carry case shown in FIG. 3.

FIG. 5 is a schematic block diagram of the mobile AED monitoring and alerting device 110. The device 110 preferably includes one or more GPS devices 114 that permit tracking of the location of the device 110, and includes structure which allows the device to send and receive signals to and from a remote host 112 (see FIG. 6). That structure may comprise a 3G module 116 and associated SIM 118 as well as an antenna 120, such as an external dipole antenna, for communication with a cellular network 122 (see FIG. 6). The device 110 may include dual SIMs 118 to enable communication with two different networks (i.e., as a backup).

The device 110 may also include an audio detector 124 (i.e., microphone and associated processor) which continuously listens for sounds and alarms being emitted from the AED 50 (via the audible alarm indicator 55 shown in FIG. 1), at least one accelerometer 126 for detecting movement of the device 110 (i.e., detecting movement of the smart carry case 100 as a whole), and a speaker or buzzer 128 for emitting an audible alarm.

The device 110 includes a controller 130 (such as a microcontroller unit (MCU)) for controlling the overall functions of the device 110. To that end, the controller 130 is effectively connected to the other components of the device.

The device 110 preferably includes a battery 132 (such as a lithium ion battery) which powers the device, as well as an associated charger and socket 134 for charging the battery 132 using either a wall socket or a vehicle's power system. All the functions of the device 110 are powered by the battery 132 rather than the battery of the AED 50.

The device 110 may include indicator lights 136, such as LED indicators, for indicating the status of operation of the device 110. The device 110 may also include one or more inputs 138 for effectively tethering the device 110 to something such that removal causes the controller 130 to determine that the device 110 has been disconnected. At that point, the remote host 112 (see FIG. 6) can be notified and/or the device 110 may emit an audible alarm using the speaker or buzzer 128. The device may include an audio vent 140 so the sound emitted by the internal buzzer 128 can be better heard.

With regard to what is communicated back to the remote host 112 (see FIG. 6), these communications can include the fact that the smart carry case 100 is low on battery 132, the battery 132 will not hold a charge, the smart carry case 100 has received an impact or its axis has changed (effectively detected by the accelerometer 126), a fault relating to the AED 50 has been detected (i.e., by the audio detector 124 by effectively hearing fault signals emitted by the AED 50), etc. The device 110 can also be configured such that any or all of these conditions also cause the buzzer 128 to emit an audio alarm.

As shown in FIG. 5, the device 110 also preferably includes external memory 141 to enable remote software updates, and an SMA antenna 143 (i.e., for sending or receiving electromagnetic waves that improves the signal required for remote communications).

Figure 6:
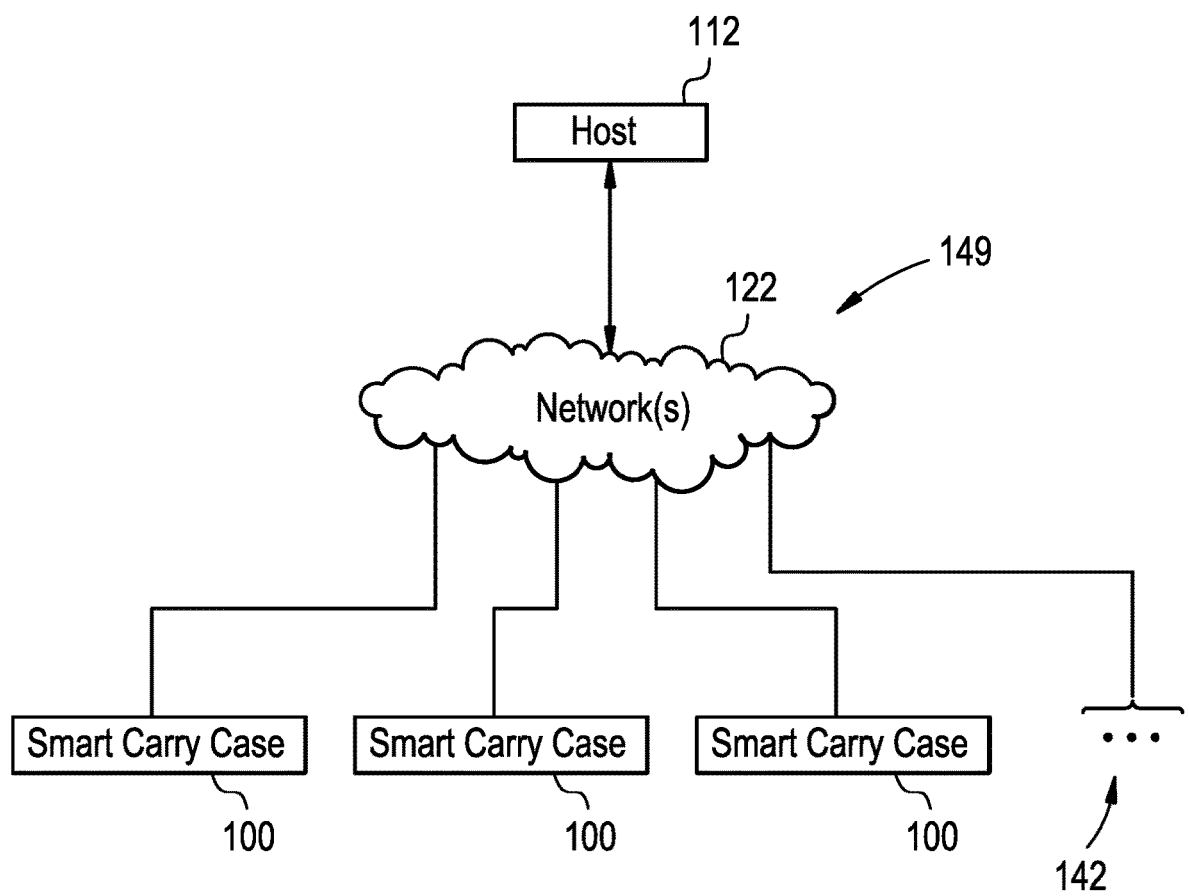
FIG. 6 is a schematic block diagram of a network of smart carry cases.

As shown in FIG. 6, the smart carry case 100 preferably exists in a network 149 of identical smart carry cases 100 wherein each smart carry case 100 can communicate with a remote host 112 via one or more networks 122 (such as cellular networks). While three smart carry cases 100 are shown in FIG. 6, of course many more can be included in the network 149 as symbolized by the dots 142.

Figure 7:
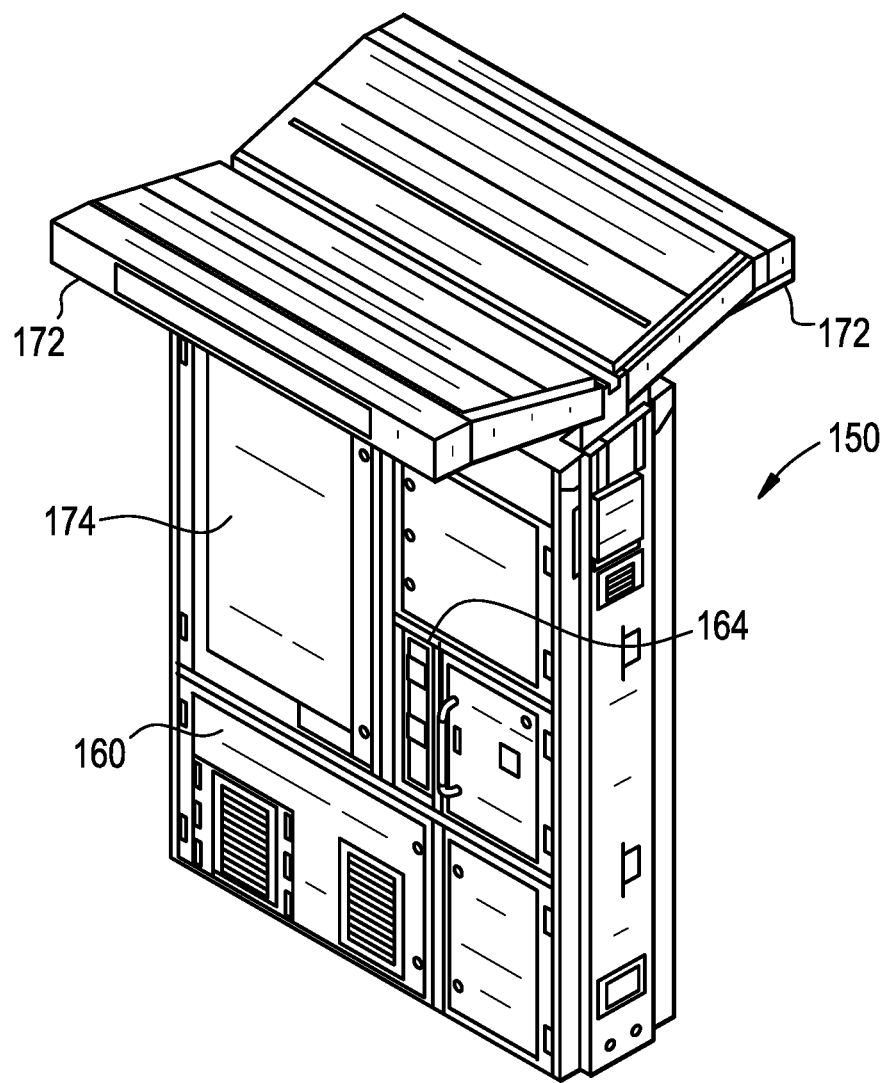
FIG. 7 is a perspective view of street furniture that is in accordance with another embodiment of the present invention.
Figure 8:
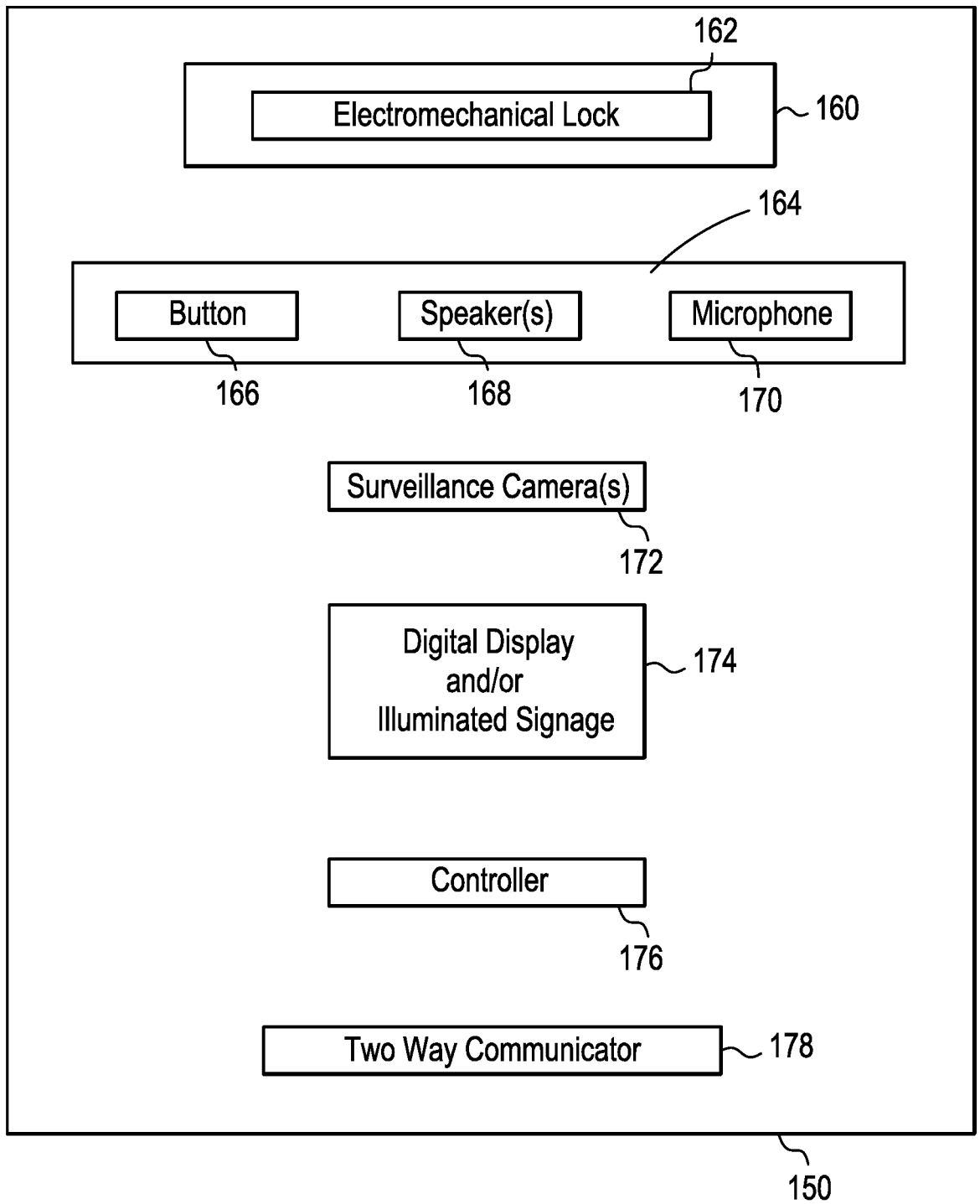
FIG. 8 is a schematic block diagram of the street furniture shown in FIG. 7.

FIG. 7 is a perspective view of street furniture 150 that is in accordance with another embodiment of the present invention, while FIG. 8 is a schematic block diagram thereof which shows some of the main components. The street furniture 150 is configured to retain, continuously monitor, and dispense an AED 50 and communicate to a remote host (i.e., a control room).

Figure 9:
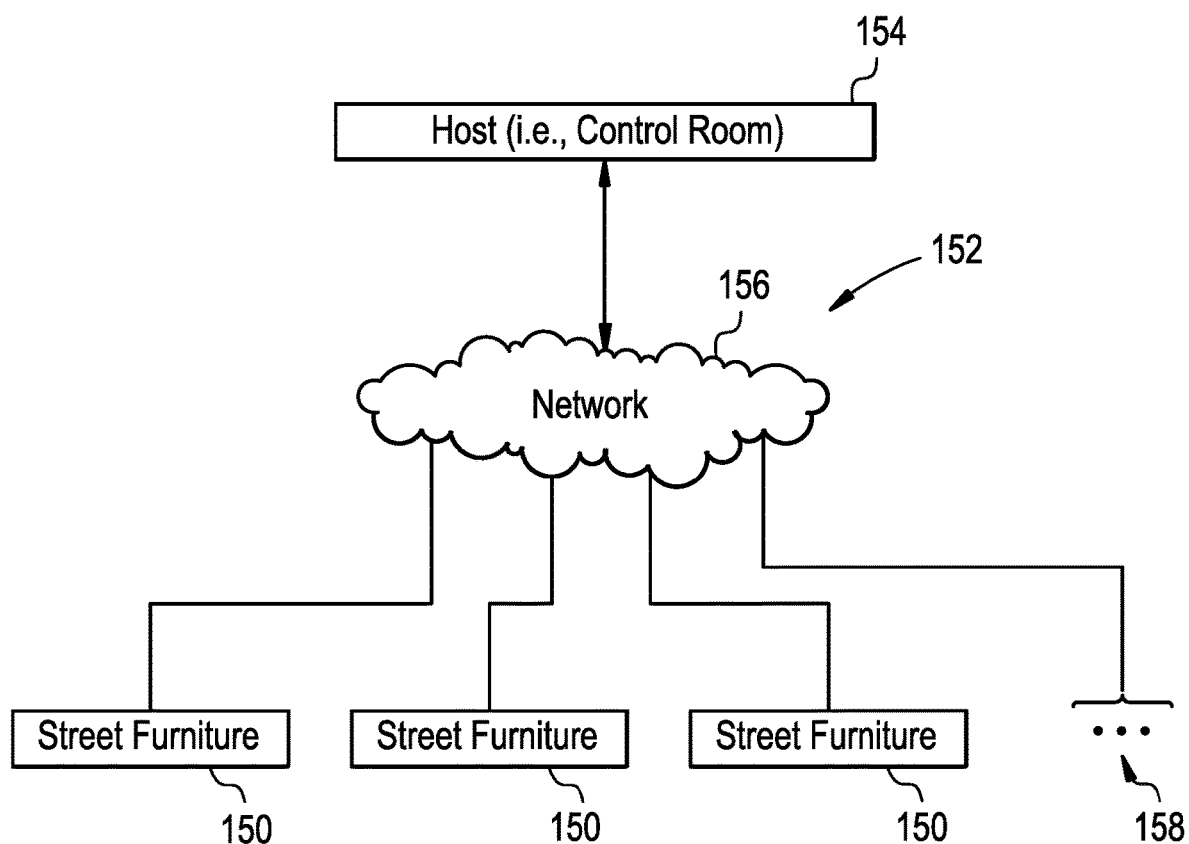
FIG. 9 is a schematic block diagram of a network of street furniture.

As shown in FIG. 9, the street furniture 150 preferably exists in a network 152 of identical street furniture 150 wherein each piece of street furniture 150 can communicate with a remote host 154 (such as control room) via one or more networks 156 (such as cellular networks). While three pieces of street furniture 150 are shown in FIG. 9, of course many more can be included in the network 152 as symbolized by the dots 158.

As shown in FIGS. 7 and 8, the street furniture 150 may include, among other components, a remotely lockable/unlockable compartment 160 (using an electromechanical lock 162 as shown in FIG. 8) for containing and dispensing the AED 50, an intercom panel 164 (i.e., a button 166, at least one speaker 168 and a microphone 170, as shown in FIG. 8), and at least one surveillance camera 172. The street furniture 150 may also include at least one digital display and/or illuminated signage 174, on the front and/or back. As shown in FIG. 8, the street furniture preferably includes a controller 176 which is connected to the components and controls the functions of the street furniture 150, and a two way communicator 178 which functions to enable the street furniture to communicate back and forth with the control room (see FIG. 9).

The street furniture 150 is preferably configured such that a user presses the intercom button 166. In response, the street furniture 150 contacts the control room 154 (see FIG. 9). The control room 154, in turn, sends a signal to the street furniture 150 causing the compartment 160 to unlock (via the electromechanical lock 162 as shown in FIG. 8) so the AED 50 can be removed and used in a rescue. If the AED 50 is used, an ambulance is deployed to the location. The street furniture 150 is configured such that the control room 154 (see FIG. 9) can effectively use the one or more surveillance cameras 172 to monitor activity at the street furniture 150. The AED 50 which is retained in the compartment 160 may be a smart carry case 100 as has been described hereinabove and shown in FIGS. 1-6. As such, the presence, function, and location of the AED 50 can be continuously monitored.

The street furniture 150, and specifically the controller 176 thereof, may be configured to unlock the compartment 160 after a set period of time after the button 166 is pressed, or in the event of power loss. The street furniture 150 may be configured such that this auto-open feature can be deactivated, such as by the control room 154.

While specific embodiments of the invention have been shown and described, it is envisioned that those skilled in the art may devise various modifications without departing from the spirit and scope of the present invention.

What is claimed is:

1. Street furniture configured to retain, continuously monitor, and dispense an Automated External Defibrillator (AED) and communicate to a remote host, said street furniture comprising an intercom button, a remotely lockable/unlockable compartment configured to contain the AED, wherein the street furniture is configured such that pressing the intercom button causes the street furniture to unlock the compartment containing the AED.

2. Street furniture as recited in claim 1, wherein the street furniture is configured to be part of a network comprising additional pieces of street furniture, wherein each piece of street furniture is configured to communicate back and forth with the remote host.

3. Street furniture as recited in claim 2, wherein the network comprises a cellular network.

4. Street furniture as recited in claim 1, wherein the remotely lockable/unlockable compartment comprises an electromechanical lock.

5. Street furniture as recited in claim 1, wherein the street furniture further comprises an intercom panel.

6. Street furniture as recited in claim 5, wherein the intercom panel comprises the intercom button, at least one speaker, and a microphone.

7. Street furniture as recited in claim 1, wherein the street furniture further comprises at least one surveillance camera.

8. Street furniture as recited in claim 1, wherein the street furniture further comprises at least one digital display.

9. Street furniture as recited in claim 1, wherein the street furniture further comprises illuminated signage.

10. Street furniture as recited in claim 1, wherein the street furniture further comprises a controller which is configured to control functions of the street furniture.

11. Street furniture as recited in claim 1, wherein the street furniture further comprises a two way communicator which functions to enable the street furniture to communicate back and forth with the remote host.

12. Street furniture as recited in claim 6, wherein the street furniture is configured to contact the remote host in response to the intercom button being pressed.

13. Street furniture as recited in claim 1, wherein the street furniture is configured receive a signal from the remote host causing the remotely lockable/unlockable compartment to unlock.

14. Street furniture as recited in claim 13, wherein the remotely lockable/unlockable compartment unlocks via the electromechanical lock so the AED can be removed from the street furniture.

15. Street furniture as recited in claim 7, wherein the street furniture is configured such that the at least one surveillance camera is usable by the remote host to monitor activity at the street furniture.

16. Street furniture as recited in claim 1, wherein the AED comprises a smart carry case wherein the presence, function, and location of the AED is continuously monitored.

17. Street furniture as recited in claim 10, wherein the street furniture further comprises an intercom panel, wherein the intercom panel comprises a button, at least one speaker, and a microphone, and wherein the controller of the street furniture is configured to unlock the remotely lockable/unlockable compartment after a set period of time after the button is pressed, or in the event of power loss.

18. Street furniture as recited in claim 10, wherein the street furniture further comprises an intercom panel, wherein the intercom panel comprises the intercom button, at least one speaker, and a microphone, wherein the controller of the street furniture is configured to provide an auto-open feature wherein the controller is configured to unlock the remotely lockable/unlockable compartment after a set period of time after the button is pressed, or in the event of power loss, and the controller is configured such that the auto-open feature can be deactivated by the remote host.

19. Street furniture as recited in claim 1, wherein the street furniture is configured to deploy an ambulance to the location of the AED upon detection that the AED has been used after having been removed from the street furniture.

20. Street furniture as recited in claim 1, further comprising a carry case in the compartment, wherein said AED is disposed in the carry case, wherein said carry case comprises a space for containing the AED, a mobile AED monitoring and alerting device separate from the AED, said AED monitoring and alerting device configured to continuously monitor at least one of a functional state and the physical state of the AED, said mobile AED monitoring and alerting device comprising a GPS device configured to track a location of the mobile AED monitoring and alerting device.

\* \* \* \* \*